United States Patent [19]

Picozza et al.

[11] Patent Number: 4,962,045

[45] Date of Patent: Oct. 9, 1990

[54] TIME-RESOLVED FLUORIMETRIC DETECTION OF LANTHANIDE LABELED NUCLEOTIDES

[75] Inventors: Enrico G. Picozza, Ridgefield; Steven S. Saavedra, New Milford, both of Conn.

[73] Assignee: The Perkin-Elmer Corporation, Norwalk, Conn.

[21] Appl. No.: 188,925

[22] Filed: May 2, 1988

[51] Int. Cl.$^5$ .......................................... G01N 33/566
[52] U.S. Cl. ................... 436/501; 436/536; 436/546; 436/800; 436/94; 436/56
[58] Field of Search ............... 436/501, 546, 800, 547, 436/536, 94, 537, 56, 805

[56] References Cited

U.S. PATENT DOCUMENTS 4,808,541  2/1989  Nikola et al. .................. 436/501

FOREIGN PATENT DOCUMENTS 195413  9/1986  European Pat. Off. .
212951  3/1987  .

OTHER PUBLICATIONS

Dechaud et al., "Laser Excited Immunofluorometric Assay of Prolactin with Use of Antibodies Coupled to Lanthanide-Labeled DTPAA", (Abstract only) Clin. Chem. 32(7), 1986 1323-1327.

Syvanen, A. C. et al., Nucl. Acids Res. 14, 1017-1028 (1986).

Bailey, N. P. et al., Analyst, 109, 1449-1450 (1984).

Bailey, N. P. et al, Analyst, 110, 603-604 (1985).

Weider, I., Background Rejection in Fluorescence Immunoassay, Immunofluorescence and Related Staining Techniques, 67-80 (1978).

Dahlen, P. Anal. Biochem., 164. 78-83 (1987).

*Primary Examiner*—Robert J. Warden
*Assistant Examiner*—Lyle A. Alexander
*Attorney, Agent, or Firm*—Thomas P. Murphy; Edwin T. Grimes

[57] ABSTRACT

Nucleotides conjugated with a chelating agent and labeled with a lanthanide, especially terbium, are readily detected by time-resolved fluorimetry during and following gel electrophoresis. The labeled nucleotide conjugates are very stable, highly fluorescent with a long radiative lifetime and remain fluorescent during dilution and during gel electrophoresis and since an enhancement solution is not required for detection, the labeled nucleotide conjugates can be detected on-line, if desired.

21 Claims, No Drawings

TIME-RESOLVED FLUORIMETRIC DETECTION OF LANTHANIDE LABELED NUCLEOTIDES

FIELD OF THE INVENTION

This invention relates to a method for time-resolved fluorimetric detection of fluorescent labeled nucleotides in a gel electrophoresis system in which there is used as fluorescent labeled nucleotides, nucleotides conjugated with a chelating agent and labeled with a lanthanide.

BACKGROUND OF THE INVENTION

The ability to detect nucleic acids or nucleotides at trace levels is required and extremely important in many areas of biotechnology. In the past, tracking and detection of nucleotides was usually performed using radioisotopes. However, these methods employing radioisotopes are generally very laborious, time-consuming, expensive, and require the use of unstable and hazardous radioisotopes leading to problems and handling and disposal of the radioisotope labeled reagents. Therefore, interest has arisen in discovering alternative and safer methods of detection.

One such alternative has been the suggestion that enzyme catalyzed color development be employed However, this proposed methodology has not found general acceptance because of a much lowered sensitivity than methods employing radiolabeled nucleotides In addition, the enzyme catalyzed methodology was found not to have any general improved ease of performance over the radiolabeled nucleotide methods.

Therefore, as another alternative, various methods of detecting nucleic acids or nucleotides based upon fluorescent emissions have been proposed or employed. Perhaps the most widely employed method involves staining with a dye such as ethidium bromide. However, due to background emission from unbound dye, the detection limits cannot approach those in autoradiography. It has been proposed that elimination of the background problem due to free dye can be achieved by covalent modification of nucleic acid with a fluorescent tag followed by separation of unreacted label. With appropriate choice of fluorophore and optimization of the optical train, sensitivities approaching or matching those of radioisotopic detection are considered to be possible Several research groups have employed this approach to detect DNA fragments in polyacrylamide gels. A drawback of this approach is that the gel is a source of significant scattering and background fluorescence.

An alternative detection scheme which is theoretically more sensitive than autoradiography is time-resolved fluorimetry. According to this method, a chelated lanthanide metal with a long radiative lifetime is attached to the molecule of interest. Pulsed excitation combined with a gated detection system allows for effective discrimination against short-lived background emission Syvanen et al., Nucleic Acids Research, 14, 1017–1028 (1986) have demonstrated the utility of this approach for quantifying DNA hybrids via an europium-labeled antibody. In addition, biotinylated DNA was measured in microtiter wells using Eu-labeled strepavidin as reported by P. Dahlen, Anal. Biochem., 164, 78–83 (1982). However, a disadvantage of these types of assays is that the label must be washed from the probe and its fluorescence developed in an enhancement solution. In addition, it has been difficult to provide sufficiently stable labeled molecules to provide for acceptable detection thereof. Moreover, in gel electrophoresis systems the labeled molecules have generally not provided sufficient stability on dilution or when subjected to the elevated temperatures of the gel electrophoresis to enable acceptable detection of the labeled molecules. A further drawback has been the fact that the fluorescence produced has only been in the nanosecond (ns) range, a generally unacceptably short period for adequate detection of the labeled molecules and for discrimination from background fluorescence.

Thus, a need has clearly arisen for fluorescent labeled nucleotides that can be employed in gel electrophoresis systems to provide long lived fluorescence to avoid background fluorescence by use of an intermittent excitation source and a timed coupled measurement of fluorescence. A still further need is to provide for such fluorescent labeled nucleotides for use in detecting nucleotides by time-resolved fluorimetric determination of such labeled nucleotides separated in a gel electrophoresis system in which the labeled nucleotide remains stable and detection limits are significantly improved in comparison to covalent labels with fluorescent lifetimes in the nanosecond range or in comparison to such system employing stains such as ethidium bromide A further need is to provide such a detection method in which the fluorescent labeled nucleotide remains stable and fluorescent upon dilution in the gel system and in an electric field at an elevated temperature of about 60° C. A still further need is to provide such a method for such time-resolved fluorimetric detection of labeled nucleotides in gel electrophoresis systems in which no enhancement solution is required for detection and thereby permitting on-line detection of the fluorescent labeled nucleotides.

SUMMARY OF THE INVENTION

A method for time-resolved fluorimetric detection of fluorescent labeled nucleotides monomers, oligomers or polymers separated in a gel electrophoresis system is provided by employing as the fluorescent labeled nucleotides lanthanide chelate labeled covalent nucleotide conjugates. The invention further provides such a method for on-line time-resolved fluorimetric detection of such fluorescent labeled nucleotides separated in gel electrophoresis systems.

DETAILED DESCRIPTION OF THE INVENTION

In accordance with this invention, time-resolved fluorimetric detection of fluorescent labeled nucleotides separated in a gel electrophoresis system is provided by employing a lanthanide chelate labeled covalent nucleotide conjugate in which the nucleotide may be a monomer, oligomer of polymer of either DNA or RNA, although for purposes of illustrating the invention the following examples and discussion relate to DNA nucleotides.

The lanthanide chelate labeled covalent nucleotide conjugates useful in the invention may be the chelate of any suitable lanthanide producing the stable lanthanide chelate of a covalent nucleotide conjugate having the properties previously described. While any suitable lanthanide chelate may be employed, it is preferred that the lanthanide be terbium, samarium, europium, dysprosium or neodymium, with terbium being the especially preferred lanthanide moiety.

The lanthanide is chelated to a nucleotide which has been covalently reacted with a strong lanthanide chelating agent. The chelating agent which is reacted with the nucleotide is any suitable chelating agent that is capable of covalently binding to a reactive group on a nucleotide and which also chelates to a fluorescent lanthanide in a stable manner so that a long-lived lanthanide chelate of the covalently bound nucleotide-chelating agent conjugate is provided. By long-lived fluorescence is meant a high quantum yield fluorescence that is not appreciably decayed when background interference has already decayed. It is also desirable that the chelating agent does not adversely affect the ability of the nucleotide to undergo hybridization.

As examples of chelating agents suitable for reaction with nucleotides to form the nucleotide conjugates suitable for chelating lanthanides, there may be mentioned, for example, amine polyacids, cryptands, polyacid substituted pyridine derivatives and the like. As examples of each chelating agents, there may be mentioned, for example, amine polyacids such as diethylenetriaminepentaacetic acid dianhydride (DTPAA), benzenediazonium ethylenediaminetetraacetic acid (EDTA), cryptands such as isothiocyanatobenzyl 2B:2:1 cryptand, and polyacid substituted pyridine derivatives such as 2,6-bis[N,N-Di(carboxymethyl)aminomethyl]-4 -(3-isothiocyanatophenyl)-pyridine tetraacid. Especially preferred as the chelating agent is DTPAA.

The chelating agent is preferably covalently bound to the nucleotide along with an energy transfer agent, preferably an aminoaromatic compound such as, for example, p-aminosalicylic acid (pAS), aminophenazone, aminomethylsalicylic acid, aniline, aminophthalic acid, 3,4-dihydroxybenzylamine, 5-aminoisophthalic acid, 5-aminophenanthroline, 3-aminobenzoic acid and the like. Preferably pAS is employed as the energy transfer moiety.

Preferably, the nucleotide conjugate to which the lanthanide is chelated is a conjugate of the formula:

Nuc-N*-Y-Z wherein Nuc is a nucleotide monomer, oligomer or polymer, N* is an amine nitrogen either intrinsic to the nucleotide or extrinsinc and introduced as a label prior to conjugation, Y is a chelating group capable of chelating a lanthanide and Z is an energy transfer moiety More preferably Y is a diethylenetriaminepentaacetic acid group and Z is a p-aminosalicylate moiety and thus the conjugate has the formula:

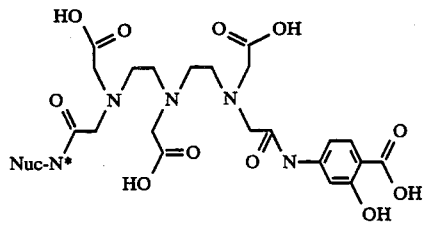

Especially preferred lanthanide chelate labeled nucleotide conjugates used in the methods of this invention are terbium chelates of nucleotide-DTPAA-pAS conjugates.

The lanthanide labeled nucleotide conjugates employed in this invention are highly fluorescent labeled conjugates with lifetime in the microsecond (ms) range. Thus, when a pulsed source and gated electronics are employed, the long-lived fluorescence decay permits effective discrimination against background fluorescence, stray light and scattered excitation. Furthermore, such lanthanide labeled nucleotide conjugates are very stable and maintain their integrity in electrophoretic gel systems and maintain their fluorescent properties upon dilution and in an electric field at elevated temperatures of about 60° C., conditions typically encountered during polyacrylamide gel electrophoresis. Moreover, such lanthanide labeled covalent nucleotide conjugates do not require enhancement solutions for detection and therefore the detection methodology may be used in situations where on-line detection is desirable or required. Since the methodology of this invention permits on-line detection of the fluorescent labeled nucleotides conjugates, the method can be employed in gel electrophoresis system for the purpose of DNA or RNA sequence determination according to the procedures of Maxam-Gilbert or Sanger, or for restriction mapping or other procedures where detection of nucleic acids is required. In addition to all of the above-mentioned advantages, the lanthanide chelates of the covalent nucleotide conjugates permit the elimination of the use of radioisotopes in the gel electrophoresis system yet provides a nucleotide detection methodology that rivals the sensitivity obtained when using radioisotope labeled nucleotides.

The invention is demonstrated by the following illustrative examples.

PREPARATION OF LANTHANIDE CHELATE LABELED NUCLEOTIDE CONJUGATES

Sodium pAS was dried overnight at 110° C. and solutions of the sodium pAS and DTPAA were prepared in dry DMSO at 0.1 M; equimolar triethylamine was added to the DTPAA solution to facilitate dissolution. An equal volume of the pAS solution was added dropwise to the DTPAA solution followed by stirring for about 60 minutes to produce a conjugate reaction mixture or chelating agent.

Separately, plasmid pBR322 was purified by centrifugation on a cesium chloride-ethidium bromide gradient and the plasmid then cleaved with HinfI restriction enzyme to produce a plasmid digest according to procedures known in the art and as described by T. Mamatis et al., Molecular Cloning: A Laboratory Manual, 100–106, Cold Spring Harbor Laboratory, Cold Spring Harbor, N.Y. HinfI digestion of pBR322 generates 10 fragments with staggered ends ranging from 75 base pairs to 1631 base pairs; the sequence of single-stranded bases at each end is ANT, where N denotes any nucleotide. It is assumed that the exocycle amines on the exposed bases provide sites for attack by the monoanhydride adduct, forming an amide linkage.

Seven uL of the conjugate reaction mixture was added to 150 μL of the plasmid digest (0.145 μg/μL cleaved pBR322) and stirred at room temperature for about 60 min. After storage overnight at 4° C., 6.8 μL of 0.05 M terbium chloride was added, the mixture was shaken and let stand for about 30 min. Excess, hydrolyzed chelate was separated from the plasmid digest chelate conjugate by two passes through a 16×1 cm column packed with Sephadex G 25-150. The elution buffer was 10 mM 3-[N-morpholino]propane sulfonic acid (MOPS) pH 7.0 After each purification, the DNA-containing fractions were pooled and evaporated to dryness under vacuum to produce the terbium labeled nucleotide conjugate.

CHARACTERIZATION OF TERBIUM LABELED DNA CONJUGATE

DNA concentration of the labeled DNA conjugate was determined by measurement of absorbencies at 260 nm. Label concentration was determined by comparing the fluorescence of the purified labeled nucleotide conjugate with the fluorescence of free chelate, i.e. diethylenetriaminepentaacetic acid dianhydride p-aminosalicylate adduct (DTPAA-pAS) complexed with terbium. The assumption inherent in this method is that the quantum yield of the conjugated label is equal to the free chelate. Correction for pAS absorption at 260 nm when measuring DNA concentration was not necessary due to the low pAS/base ratio. Spectral measurements were performed with a Perkin-Elmer Lambda Array UV-VIS spectrometer and a Perkin-Elmer LS-5 spectrofluorimeter; the latter employs a pulsed source and gated detection electronics, permitting selective observation of delayed emission. Samples were excited at 260 nm and detected at 545 nm using 10 nm slits; the delay between excitation and detection was 0.1 ms while the gate was 6 ms.

The extent of chelate incorporation into the purified DNA conjugate was calculated to be 6.3 pmol per ug of DNA.

The quantum yield of the free chelate was estimated using the relation $$\frac{Q_c}{Q_{qs}} = \frac{F_c * A_c}{F_{qs} * A_{qs}}$$

where $Q_c$ and $Q_{qs}$ are the quantum yields of the free chelate and quinine sulfate, respectively; $F_c$ and $F_{qs}$ are the areas under the corrected emission spectra; and $A_c$ and $A_{qs}$ are the absorbances at the respective excitation wavelengths. $Q_{qs}$ was taken as 0.59 at 347 nm excitation. Quinine sulfate fluorescence was measured without a time delay between excitation and detection while free chelate fluorescence was measured with the delay and gate settings listed above. Although measurement of standard and sample emission under different instrumental conditions affects the accuracy of the estimated $Q_c$, this prevented calculating an artificially low value due to the delayed fluorescence of the label.

Lifetimes were determined by measuring the emission intensity as a function of the time delay between excitation and detection, holding the gate constant. The data were fit to the best single exponential of the form $$I = I_o e^{-kt}.$$

The emission spectra of the purified terbium labeled nucleotide conjugate is characteristic of the terbium ion, with the maximum intensity occurring at 545 nm. The excitation spectrum closely matches the absorption spectrum of pAS consistent with the understanding that the terbium emission is not excited directly but is due to energy transfer from the salicylate group. At the concentrations employed, terbium fluorescence could not be detected in the absence of the DTPAA-pAS adduct. Detection was also not possible in the presence of pAS and hydrolyzed DTPAA (no adduct formation).

The quantum yield of the free chelate was estimated to be 0.09 at room temperature, which is appreciable for such a long-lived fluorophore; the molar absorptivity is 17900 $M^{-1}cm^{-1}$ at 260 nm. It is assumed that the spectral properties of the free chelate are similar to that of the chelate coupled to DNA since the excitation and emission spectra are substantially identical. Time-resolved emission measurements of the free chelate and the DNA-chelate conjugate yielded fluorescence lifetimes of 1.7 and 1.5 ms, respectively. Thus, when gated electronics are employed to discriminate against short-lived scattering and background fluorescence, detection of the chelate will be possible at very low levels. An emission scan (60 nm/min) of a 1 nM solution of the free chelate using the standard conditions listed above gave a signal-to-noise ratio of 64 at 545 nm.

GEL ELECTROPHORESIS AND TERBIUM LABELED NUCLEOTIDE CONJUGATE DETECTION

The terbium labeled nucleotide conjugates (labeled restriction fragments) prepared according to the foregoing described preparation were electrophoresed on a 1.5 mm × 16 cm, 5% polyacrylamide gel in pH 8.0 Tris-borate buffer (0.089 M, without EDTA). The polyacrylamide gel was of the following formulation:

| | |
|---|---|
| 40 ml | Deionized Water |
| 4.81 g | Acrylamide |
| 0.17 g | Bis-acrylamide |
| 42 g | Urea |
| 10 ml | 10X Sequencing Buffer* |
| 0.66 ml | 10% Ammonium Persulfate |
| 0.060 ml | TEMED |

Deionized Water to 100 mls
*10X Sequencing Buffer 500 mM Tris Base, 500 mM Boric Acid.

The system was run at 8 V/cm until the bromophenol blue tracking dye was approximately 2 cm from the bottom of the gel. The gel was then removed from the apparatus and transilluminated (Fotodyne, Model 3-3000) to locate the labeled DNA fragments. The portions of gel containing the DTPAA-pAS-Tb-labeled DNA plasmid digest, identified by the characteristic green emission, were cut out of the gel and placed individually in centrifuge tubes with 1 mL of deionized water. After storage at 4° C. for 6 days, the supernatants were separated from the gel fragments, diluted up to a final volume of 1.5 mL, and assayed for chelate emission.

The time-resolved fluorescence intensity of the gel extracts was measured on a Perkin-Elmer Model LS-5 spectrofluorimeter under the following conditions: slit widths, 10 nm; excitation wavelength, 260 nm; emission wavelength, 545 nm; time delay from excitation to observation, 0.1 ms; duration of observation gate, 6 ms. All extracts were diluted to a final volume of 1.5 mL before measurement. The absolute intensity values recorded for the eight fractions of the gel (labeled restriction fragments were extracted from eight pieces of the gel) are listed in the following table. The order of the fractions is from least mobile (top of the gel) to most mobile (bottom of the gel).

TABLE I

| Gel Fraction | Fluorescence Intensity (absolute intensity value) | pmol of Label |
|---|---|---|
| 1 | 47.7 | 18.9 |
| 2 | 51.5 | 16.6 |
| 3 | 43.9 | 8.2 |
| 4 | 41.4 | 5.2 |
| 5 | 45.3 | 9.8 |
| 6 | 4.7 | 9.1 |
| 7 | 42.0 | 5.9 |

TABLE I-continued

| Gel Fraction | Fluorescence Intensity (absolute intensity value) | pmol of Label |
|---|---|---|
| 8 | 37.9 | 1.1 |

The measured fluorescence intensity values were converted to the amounts of the fluorescent label, DTPAA-pAS-Tb, attached to pBR322 restriction fragments in each gel fraction through a calibration curve. The calibration curves was constructed by measuring the fluorescence intensity from serial dilutions of the hydrolyzed adduct complexed with terbium (free chelate) under the same instrumental conditions as the labeled restriction fragments. The results of those measurements are shown in the following Table II.

TABLE II

| Free Chelate (nmol/liter) | Fluorescence Intensity |
|---|---|
| 0 | 37.0 |
| 8.33 | 43.8 |
| 16.67 | 51.3 |
| 25.00 | 58.5 |
| 33.33 | 65.2 |

These data were plotted and fit by a least squares algorithm to a line described by the equation fluorescence intensity $=36.94+0.8532\times$concentration (in nmol/liter). The equation allows the conversion of the intensity values in Table I to concentrations. For example, gel fraction 1 contains $47.7 - 36.94/0.8532 = 12.6$ nmol/liter of the label attached to pBR322 fragments. The volume of each gel extract was 0.0015 liter. Therefore, the amount of label attached to pBR322 fragments in fraction 1 is 12.6 nmol/liter$\times$0.0015 liter$=$0.0189 nmol or 18.9 pmol. The amount for each gel fraction is set forth in the third column of Table I above.

The mass of labeled restriction fragments applied to the gel was 20.7 μg. Characterization of the labeled restriction fragments prior to electrophoresis showed that this mass of DNA carried 130 pmol of fluorescence label. Summing column 3 in Table I reveals that 74.8 pmol of label were recovered from the gel by the extraction procedure. Therefore, the percentage of label (and DNA) recovered from the gel is 100 $\times$74.8 pmol/130 pmol$=$58%.

STABILITY OF LABELED DNA FRAGMENTS SUBJECTED TO POLYACRYLAMIDE GEL ELECTROPHORESIS

The Tb-labeled double stranded DNA fragments were subjected to polyacrylamide gel electrophoresis to determine if the integrity of the conjugated complex could be maintained at elevated temperature in an electric field. Transillumination of the gel at room temperature after polyacrylamide gel electrophoresis permitted visualization of the characteristic green emission of the conjugated DNA. The DNA bands were extracted from the gel in the same manner as previously described and the chelate content was quantified by time-resolved fluorimetry. The total fluorescence recovered from the gel corresponded to 75 pmol of chelate (12 μg of DNA), representing 58% of the amount applied to the gel.

The effect of temperature on the quantum efficiency of the free DTPAA-pAS chelate was examined in a separate experiment. DTPAA-pAS-Tb was added to an 8% polyacrylamide gel before polymerization; cross-linking was allowed to take place in a standard 1 cm quartz cuvet. Fluorescence spectra acquired with the cuvet thermostated at 25° C. and 60° C. showed that 20% of the fluorescence intensity of the free chelate was retained with the temperature increase and said fluorescence remained detectable.

What is claimed is:

1. In a method of time-resolved fluorimetric detection of fluorescent labeled nucleotide monomers, oligomers or polymers separated in a gel electrophoresis system the improvement wherein the fluorescent labeled nucleotide is a lanthanide chelate labeled covalent nucleotide conjugate and no enhancement solution is required for detection.

2. A method according to claim 1 wherein the gel electrophoresis system is a polyacrylamide gel system.

3. A method according to claim 1 wherein the detecting of labeled nucleotides is for DNA or RNA sequencing.

4. A method according to claim 1 wherein the detecting of labeled nucleotides is by on-line detection in the gel electrophoresis system.

5. A method according to claim 1 wherein the nucleotide conjugate has the formula:

Nuc-N*-Y-Z wherein Nuc is a nucleotide monomer, oligomer or polymer, N* is an amine nitrogen either intrinsic to the nucleotide or extrinsinc and introduced as a label prior to conjugation, Y is a chelating group capable of chelating a lanthanide and Z is an energy transfer moiety, and the lanthanide chelated to said nucleotide conjugate is selected from the group consisting of terbium, samarium, europium, dysoprosium or neodymium.

6. A method according to claim 5 wherein the gel electrophoresis system is a polyacrylamide gel system.

7. A method according to claim 5 wherein the detecting of labeled nucleotides is for DNA or RNA sequencing.

8. A method according to claim 5 wherein the detecting of labeled nucleotides is by on-line detection in the gel electrophoresis system.

9. A method according to claim 5 wherein the nucleotide conjugate has the formula:

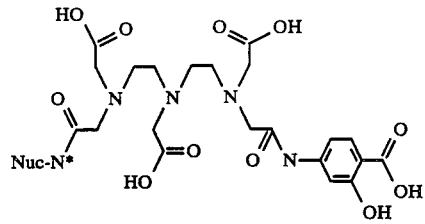

and the lanthanide chelated thereto is terbium.

10. A method according to claim 9 wherein the gel electrophoresis system is a polyacrylamide gel system.

11. A method according to claim 9 wherein the detecting of labeled nucleotides is for DNA or RNA sequencing.

12. A method according to claim 9 wherein the detecting of labeled nucleotides is by on-line detecting in the gel electrophoresis system.

13. In a method of separating fluorescent labeled nucleotide monomers, oligomers or polymers in a gel electrophoresis system the improvement wherein the fluorescent labeled nucleotide is a lanthanide chelate labeled covalent nucleotide conjugate and no enhancement solution is required for detection.

14. A method according to claim 13 wherein the gel electrophoresis system is a polyacrylamide gel system.

15. A method according to claim 13 wherein the nucleotides are separated for DNA or RNA sequencing.

16. A method according to claim 13 wherein the nucleotide conjugate has the formula:

Nuc-N*-Y-Z wherein Nuc is a nucleotide monomer, oligomer or polymer, N* is an amine nitrogen either intrinsic to the nucleotide or extrinsinc and introduced as a label prior to conjugation, Y is a chelating group capable of chelating a lanthanide and Z is an energy transfer moiety, and the lanthanide chelated to said nucleotide conjugate is selected from the group consisting of terbium, samarium, europium, dysprosium or neodymium.

17. A method according to claim 16 wherein the gel electrophoresis system is a polyacrylamide gel system.

18. A method according to claim 16 wherein the nucleotides are separated for DNA or RNA sequencing.

19. A method according to claim 16 wherein the nucleotide conjugate has the formula:

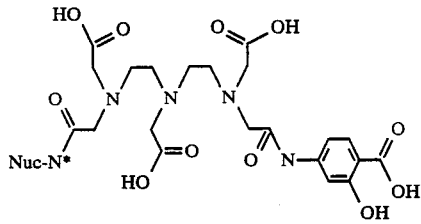

and the lanthanide chelated thereto is terbium.

20. A method according to claim 19 wherein the gel electrophoresis system is a polyacrylamide gel system.

21. A method according to claim 19 wherein the nucleotides are separated for DNA or RNA sequencing.

* * * * *